(12) United States Patent
Hodorek et al.

(10) Patent No.: US 7,842,039 B2
(45) Date of Patent: Nov. 30, 2010

(54) METHOD AND APPARATUS FOR ACHIEVING CORRECT LIMB ALIGNMENT IN UNICONDYLAR KNEE ARTHROPLASTY

(75) Inventors: Robert A. Hodorek, Warsaw, IN (US); Adam H. Sanford, Warsaw, IN (US); Richard V. Williamson, Ana Cortes, WA (US); Paul V. Saenger, Asheville, NC (US); Toby N. Farling, Warsaw, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 618 days.

(21) Appl. No.: 11/456,303

(22) Filed: Jul. 10, 2006

(65) Prior Publication Data

US 2006/0241637 A1    Oct. 26, 2006

Related U.S. Application Data

(62) Division of application No. 10/305,697, filed on Nov. 27, 2002, now Pat. No. 7,094,241.

(51) Int. Cl.
*A61F 5/00* (2006.01)
(52) U.S. Cl. ........................................................ 606/87
(58) Field of Classification Search ................ 128/898; 606/79–80, 86 R, 87–89, 96
See application file for complete search history.

(56) References Cited

U.S. PATENT DOCUMENTS

| | | | |
|---|---|---|---|
| 2,697,433 A | 12/1954 | Zehnder | |
| 3,532,088 A | 10/1970 | Fiore | |
| 4,349,018 A | 9/1982 | Chambers | |
| 4,457,307 A * | 7/1984 | Stillwell | 606/88 |
| 4,524,766 A * | 6/1985 | Petersen | 606/88 |

(Continued)

FOREIGN PATENT DOCUMENTS

DE    20202615 U1    6/2002

(Continued)

OTHER PUBLICATIONS

The Australian Office Action mailed Nov. 1,2007 in related Australian application No. 2003264612.

(Continued)

*Primary Examiner*—Anu Ramana
(74) *Attorney, Agent, or Firm*—Baker & Daniels LLP

(57) ABSTRACT

A method and apparatus for linking the distal femoral cut and the proximal tibial cut in unicondylar knee arthroplasty is disclosed. A spacing apparatus is positioned in the relevant knee compartment and utilized to hold the knee in position to correct limb alignment. The spacing apparatus includes a femoral cut slot through which the distal femoral cut is made and further includes tibial affixment apertures through which a headless securing device can be positioned to secure the spacing apparatus to the tibia. After the distal femoral resection is complete, the spacing apparatus is removed, with the headless securing devices remaining positioned in the tibia. The headless securing devices are used as a reference for securing a tibial cut block to the tibia for making the proximal tibial resection. With the mechanism of the present invention, the knee can be placed in flexion when making the proximal tibial cut.

6 Claims, 12 Drawing Sheets

U.S. PATENT DOCUMENTS

| | | | |
|---|---|---|---|
| 4,566,448 A | 1/1986 | Rohr, Jr. | |
| 4,567,885 A * | 2/1986 | Androphy | 606/88 |
| 4,567,886 A | 2/1986 | Petersen | |
| 4,574,794 A | 3/1986 | Cooke et al. | |
| 4,646,729 A | 3/1987 | Kenna et al. | |
| 4,738,253 A | 4/1988 | Buechel et al. | |
| 4,759,350 A * | 7/1988 | Dunn et al. | 606/82 |
| 4,787,383 A * | 11/1988 | Kenna | 606/88 |
| 4,825,857 A | 5/1989 | Kenna | |
| 4,841,975 A | 6/1989 | Woolson | |
| 4,938,762 A | 7/1990 | Wehrli | |
| 4,952,213 A | 8/1990 | Bowman et al. | |
| 5,002,547 A | 3/1991 | Poggie et al. | |
| 5,007,912 A * | 4/1991 | Albrektsson et al. | 606/88 |
| 5,007,936 A | 4/1991 | Woolson | |
| 5,116,338 A | 5/1992 | Walker | |
| 5,122,144 A | 6/1992 | Bert | |
| 5,213,112 A | 5/1993 | Nniwa et al. | |
| 5,230,338 A | 7/1993 | Allen et al. | |
| 5,234,433 A * | 8/1993 | Bert et al. | 606/88 |
| 5,250,050 A | 10/1993 | Poggie et al. | |
| 5,251,127 A | 10/1993 | Raab | |
| 5,275,603 A | 1/1994 | Ferrante et al. | |
| 5,305,203 A | 4/1994 | Raab | |
| 5,306,276 A | 4/1994 | Johnson et al. | |
| 5,342,367 A | 8/1994 | Ferrante et al. | |
| 5,342,368 A | 8/1994 | Petersen | |
| 5,344,423 A | 9/1994 | Dietz et al. | |
| 5,364,401 A | 11/1994 | Ferrante et al. | |
| 5,364,402 A | 11/1994 | Mumme et al. | |
| 5,368,552 A | 11/1994 | Williamson et al. | |
| 5,445,640 A | 8/1995 | Johnson et al. | |
| 5,451,228 A | 9/1995 | Johnson et al. | |
| 5,458,645 A | 10/1995 | Bertin | |
| 5,474,559 A | 12/1995 | Bertin et al. | |
| 5,484,446 A | 1/1996 | Burke et al. | |
| 5,486,180 A | 1/1996 | Dietz et al. | |
| 5,514,139 A | 5/1996 | Goldstein et al. | |
| 5,514,143 A * | 5/1996 | Bonutti et al. | 606/88 |
| 5,527,316 A | 6/1996 | Stone et al. | |
| 5,540,696 A | 7/1996 | Booth, Jr. et al. | |
| 5,551,429 A | 9/1996 | Fitzpatrick et al. | |
| 5,562,674 A | 10/1996 | Stalcup et al. | |
| 5,593,411 A | 1/1997 | Stalcup et al. | |
| 5,597,379 A | 1/1997 | Haines et al. | |
| 5,601,563 A | 2/1997 | Burke et al. | |
| 5,601,566 A * | 2/1997 | Dance et al. | 606/88 |
| 5,611,802 A | 3/1997 | Samuelson et al. | |
| 5,628,750 A | 5/1997 | Whitlock et al. | |
| 5,643,272 A | 7/1997 | Haines et al. | |
| 5,649,928 A * | 7/1997 | Grundei | 606/88 |
| 5,669,914 A * | 9/1997 | Eckhoff | 606/88 |
| 5,681,316 A | 10/1997 | DeOrio et al. | |
| 5,681,320 A | 10/1997 | McGuire | |
| 5,682,886 A | 11/1997 | Delp et al. | |
| 5,683,397 A | 11/1997 | Vendrely et al. | |
| 5,688,280 A | 11/1997 | Booth, Jr. | |
| 5,704,941 A | 1/1998 | Jacober et al. | |
| 5,735,904 A | 4/1998 | Pappas | |
| 5,743,915 A | 4/1998 | Bertin et al. | |
| 5,755,803 A | 5/1998 | Haines et al. | |
| 5,776,201 A | 7/1998 | Colleran et al. | |
| 5,788,700 A * | 8/1998 | Morawa et al. | 606/88 |
| 5,800,438 A | 9/1998 | Tuke et al. | |
| 5,810,827 A | 9/1998 | Haines et al. | |
| 5,824,085 A | 10/1998 | Sahay et al. | |
| 5,860,980 A * | 1/1999 | Axelson et al. | 606/88 |
| 5,871,018 A | 2/1999 | Delp et al. | |
| 5,879,354 A | 3/1999 | Haines et al. | |
| 5,904,691 A | 5/1999 | Barnett et al. | |
| 5,911,723 A * | 6/1999 | Ashby et al. | 606/88 |
| 5,921,992 A | 7/1999 | Costales et al. | |
| 5,995,738 A | 11/1999 | DiGioia, III et al. | |
| 6,002,859 A | 12/1999 | DiGioia, III et al. | |
| 6,033,415 A | 3/2000 | Mittelstadt et al. | |
| 6,051,016 A | 4/2000 | Mesaros et al. | |
| 6,056,754 A | 5/2000 | Haines et al. | |
| 6,077,270 A | 6/2000 | Katz | |
| 6,090,114 A | 7/2000 | Matsuno et al. | |
| 6,167,145 A | 12/2000 | Foley et al. | |
| 6,197,064 B1 | 3/2001 | Haines et al. | |
| 6,267,762 B1 | 7/2001 | Millard et al. | |
| 6,285,902 B1 | 9/2001 | Kienzle, III et al. | |
| 6,296,646 B1 | 10/2001 | Williamson | |
| 6,396,939 B1 | 5/2002 | Hu et al. | |
| 6,402,762 B2 | 6/2002 | Hunter et al. | |
| 6,430,434 B1 | 8/2002 | Mittelstadt | |
| 6,450,978 B1 | 9/2002 | Brosseau et al. | |
| 6,475,228 B1 | 11/2002 | Mesaros et al. | |
| 6,477,400 B1 | 11/2002 | Barrick | |
| 6,478,799 B1 * | 11/2002 | Williamson | 606/90 |
| 6,490,467 B1 | 12/2002 | Bucholz et al. | |
| 6,503,254 B2 | 1/2003 | Masini | |
| 6,514,259 B2 | 2/2003 | Picard et al. | |
| 6,551,325 B2 | 4/2003 | Neubauer et al. | |
| 6,554,837 B1 | 4/2003 | Hauri et al. | |
| 6,575,980 B1 | 6/2003 | Robie et al. | |
| 6,595,997 B2 | 7/2003 | Axelson, Jr. et al. | |
| 6,632,225 B2 | 10/2003 | Sanford et al. | |
| 6,685,711 B2 | 2/2004 | Axelson, Jr. et al. | |
| 6,695,848 B2 | 2/2004 | Haines | |
| 6,712,824 B2 | 3/2004 | Millard et al. | |
| 6,770,077 B2 | 8/2004 | Van Zile et al. | |
| 6,859,661 B2 | 2/2005 | Tuke | |
| 6,932,823 B2 | 8/2005 | Grimm et al. | |
| 7,029,477 B2 | 4/2006 | Grimm | |
| 7,094,241 B2 | 8/2006 | Hodorek et al. | |
| 7,201,755 B2 | 4/2007 | Faoro | |
| 7,235,080 B2 | 6/2007 | Hodorek | |
| 7,335,206 B2 | 2/2008 | Steffensmeier et al. | |
| 7,371,240 B2 | 5/2008 | Pinczewski et al. | |
| 2002/0068942 A1 | 6/2002 | Neubauer et al. | |
| 2002/0133160 A1 | 9/2002 | Axelson, Jr. et al. | |
| 2002/0133162 A1 | 9/2002 | Axelson, Jr. et al. | |
| 2002/0133163 A1 | 9/2002 | Axelson, Jr. et al. | |
| 2002/0133164 A1 | 9/2002 | Williamson | |
| 2002/0198530 A1 | 12/2002 | Farling | |
| 2003/0069585 A1 | 4/2003 | Axelson, Jr. et al. | |
| 2003/0069591 A1 | 4/2003 | Carson et al. | |
| 2003/0100906 A1 | 5/2003 | Rosa et al. | |
| 2003/0216741 A1 | 11/2003 | Sanford et al. | |
| 2003/0225413 A1 | 12/2003 | Sanford et al. | |
| 2003/0233149 A1 | 12/2003 | Hodorek | |
| 2004/0039396 A1 | 2/2004 | Couture et al. | |
| 2004/0087960 A1 | 5/2004 | Kinnett | |
| 2004/0102785 A1 | 5/2004 | Hodorek | |
| 2004/0122305 A1 | 6/2004 | Grimm et al. | |
| 2004/0152955 A1 | 8/2004 | McGinley et al. | |
| 2004/0153062 A1 | 8/2004 | McGinley et al. | |
| 2004/0249387 A1 | 12/2004 | Faoro | |
| 2005/0070910 A1 | 3/2005 | Keene | |
| 2005/0143746 A1 | 6/2005 | Steffensmeier et al. | |
| 2005/0182415 A1 | 8/2005 | Steffensmeier et al. | |
| 2005/0203528 A1 | 9/2005 | Couture et al. | |
| 2005/0203541 A1 | 9/2005 | Steffensmeier et al. | |
| 2006/0030855 A1 | 2/2006 | Haines | |
| 2006/0036257 A1 | 2/2006 | Steffensmeier et al. | |
| 2006/0149276 A1 | 7/2006 | Grimm | |
| 2006/0155293 A1 | 7/2006 | McGinley et al. | |
| 2006/0189998 A1 | 8/2006 | Rasmussen | |
| 2006/0195111 A1 | 8/2006 | Couture | |
| 2006/0217734 A1 | 9/2006 | Sanford et al. | |

| | | | |
|---|---|---|---|
| 2007/0173854 A1 | 7/2007 | Berger | |

FOREIGN PATENT DOCUMENTS

| | | | |
|---|---|---|---|
| DE | 20303498 U1 | 7/2003 | |
| EP | 0104732 A1 | 4/1984 | |
| EP | 00709061 A1 | 5/1996 | |
| EP | 00809969 B1 | 10/2002 | |
| EP | 0839501 B1 | 3/2003 | |
| EP | 1424042 B1 | 6/2004 | |
| EP | 1579812 A1 | 9/2005 | |
| FR | 2648699 | 6/1989 | |
| FR | 2679766 A1 | 2/1993 | |
| FR | 2776176 A1 | 9/1999 | |
| FR | 2819168 | 7/2002 | |
| FR | 2819168 A1 | 7/2002 | |
| JP | 1-250250 A | 10/1989 | |
| JP | 6-038971 A | 2/1994 | |
| JP | 8-229058 A1 | 9/1996 | |
| WO | WO01/66021 A1 | 9/2001 | |
| WO | WO01/85038 A1 | 11/2001 | |
| WO | WO2004/017842 A2 | 3/2004 | |
| WO | WO2004/019792 A1 | 3/2004 | |

OTHER PUBLICATIONS

The European Search Report mailed Jan. 4, 2004 in related European application No. 03257497.2.
The Canadian Office Action mailed Dec. 30, 2009 in related Canadian application No. 2,449,336.
Office Action mailed Apr. 1, 2009 in related U.S. Appl. No. 11/456,310.

* cited by examiner

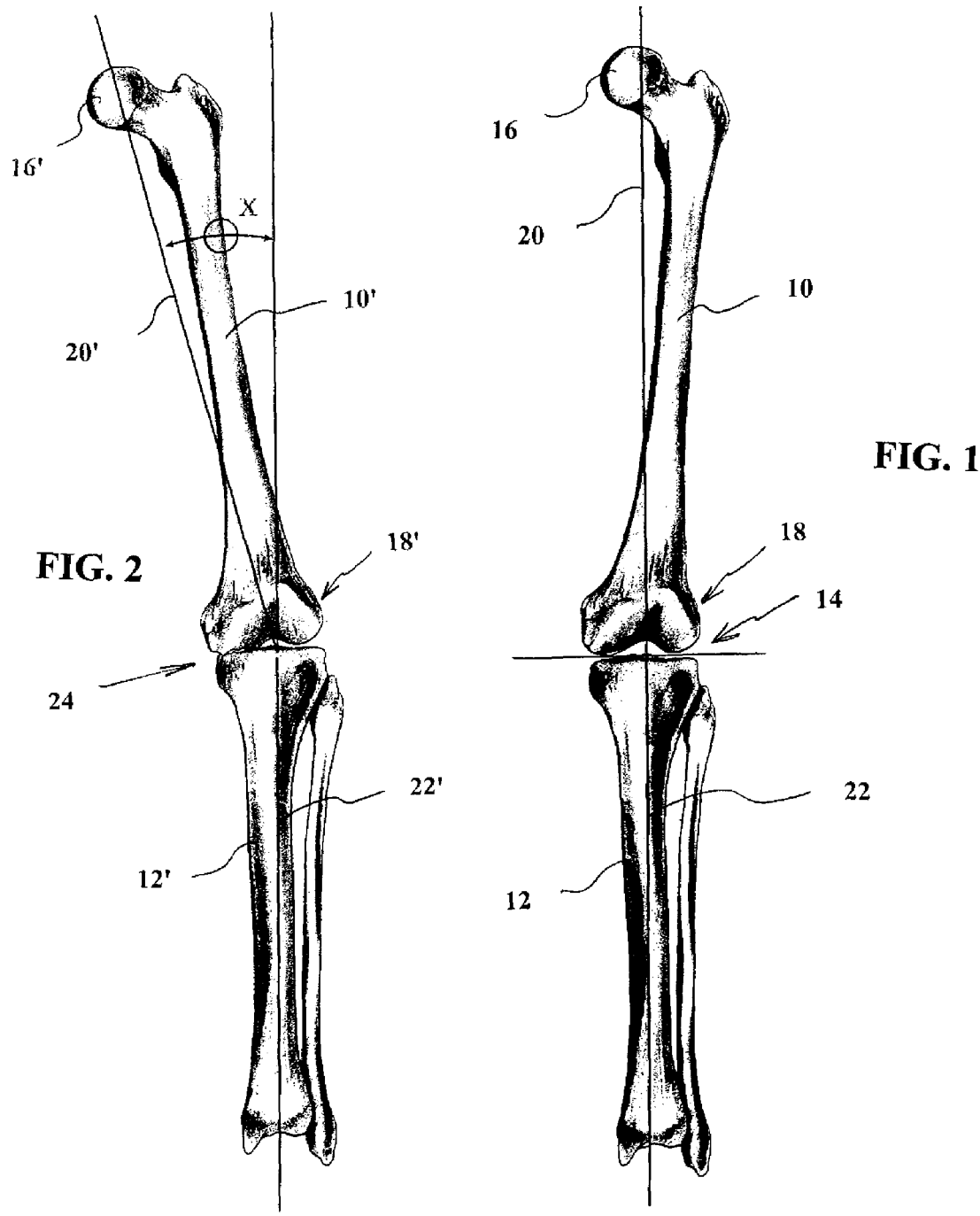

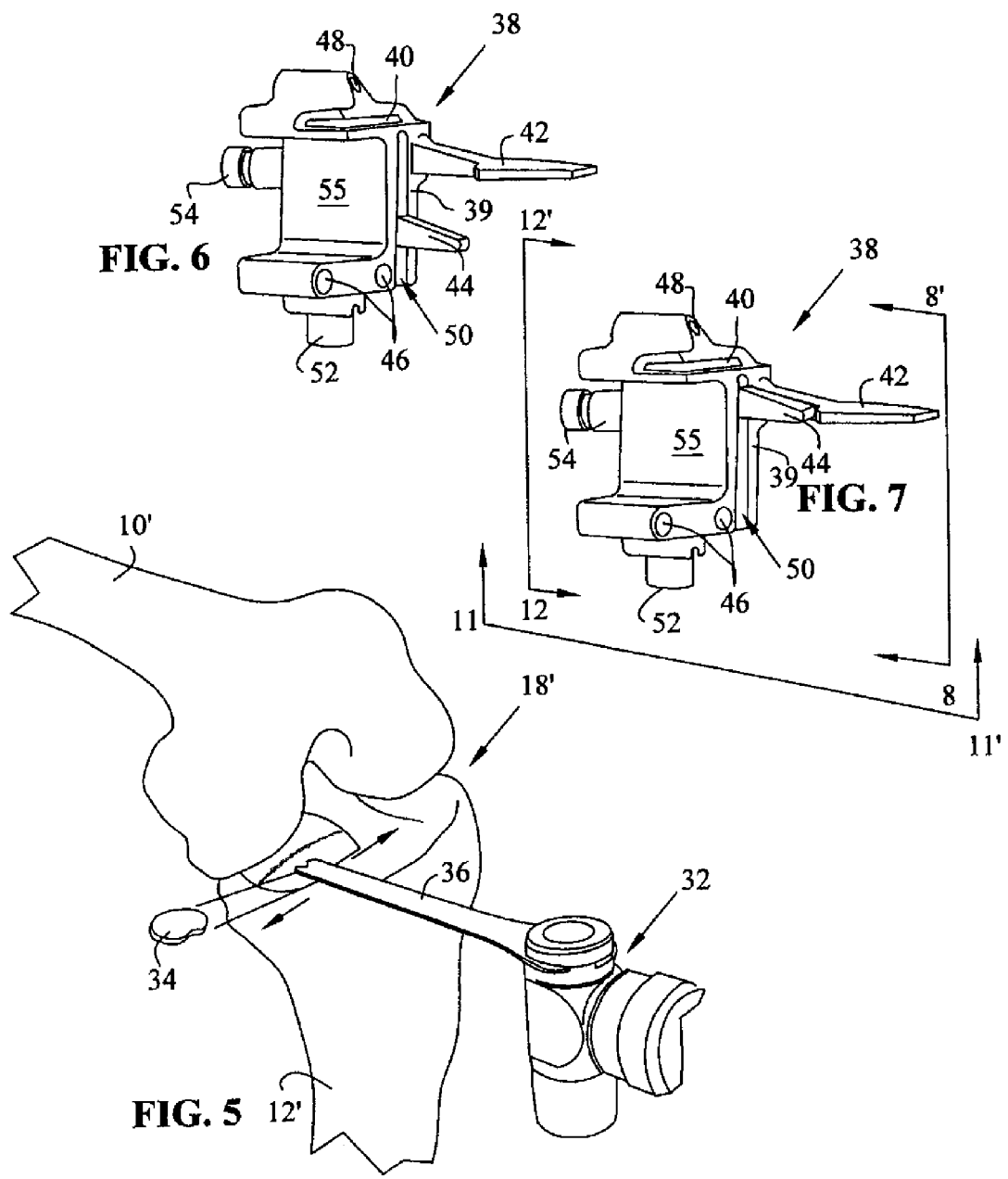

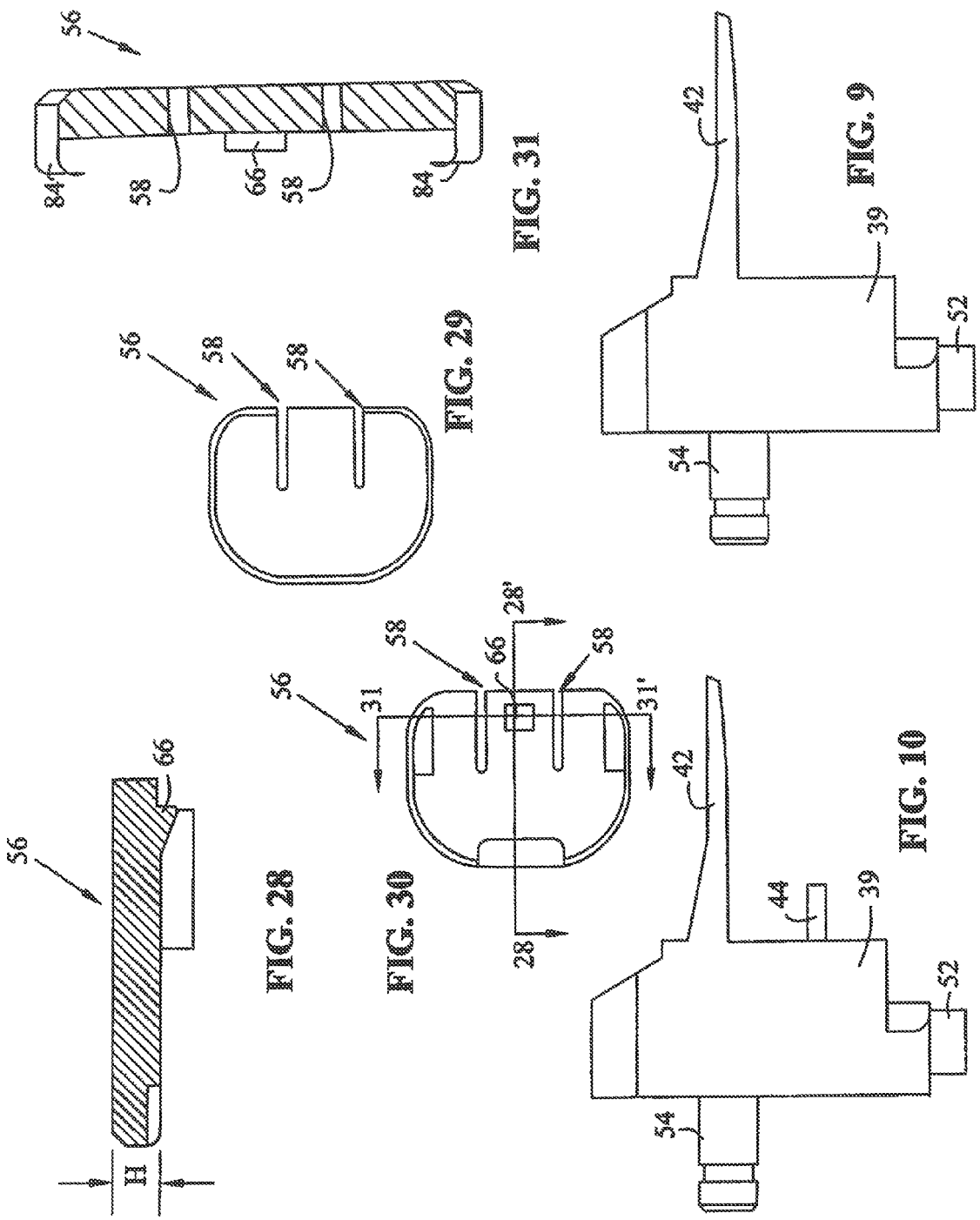

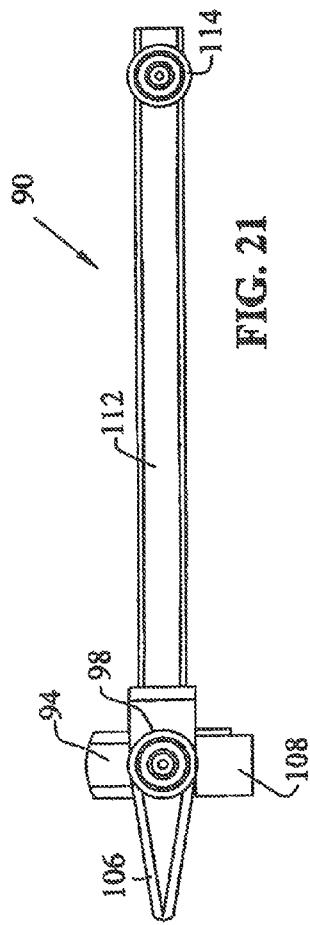
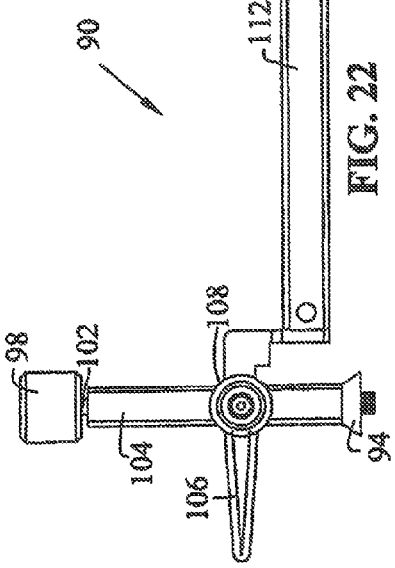
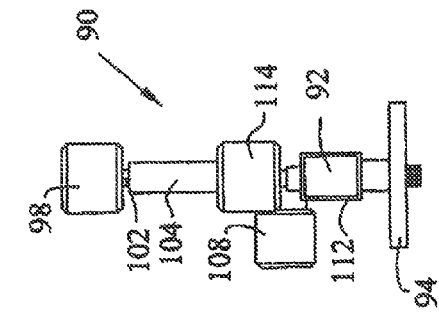
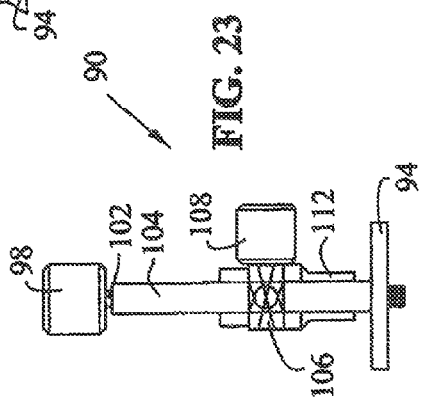
FIG. 21
FIG. 22
FIG. 23
FIG. 24

METHOD AND APPARATUS FOR ACHIEVING CORRECT LIMB ALIGNMENT IN UNICONDYLAR KNEE ARTHROPLASTY

CROSS REFERENCE TO RELATED APPLICATIONS

This application is a Divisional of U.S. application Ser. No. 10/305,697, entitled METHOD AND APPARATUS FOR ACHIEVING CORRECT LIMB ALIGNMENT IN UNICONDYLAR KNEE ARTHROPLASTY, filed on Nov. 27, 2002.

BACKGROUND OF THE INVENTION

1. Field of the Invention

The present invention relates to unicondylar knee arthroplasty, and, more particularly, to a method and apparatus for achieving correct limb alignment and linking the distal femoral cut to the proximal tibial cut in unicondylar knee arthroplasty, including minimally invasive unicondylar knee arthroplasty.

2. Description of the Related Art

Orthopedic procedures for the replacement of all, or a portion of, a patient's joint have been developed over the last thirty years. Currently, the procedures used to prepare the bone and seat the implants are generally referred to as open procedures. For the purposes of this discussion, the term "open procedure" will refer to a procedure wherein an incision is made through the skin and underlying tissue to fully expose a large portion of the particular joint surface. In both total and unicondylar knee arthroplasty, the typical incision for an open procedure is about 8-10 inches long. After the initial incision in the skin, the internal wound may be enlarged to fully expose the areas to be prepared. While this approach provides surgeons with an excellent view of the bone surface, the underlying damage to the soft tissue, including the muscles can lengthen a patient's rehabilitation time after surgery. While the implants may be well fixed at the time of surgery, it may be several weeks or perhaps months before the tissues violated during surgery are fully healed.

Unicompartmental knee arthroplasty is typically utilized to correct a varus or a valgus deformity caused by, e.g., osteoarthritis affecting the medial (a varus deformity) or lateral (a valgus deformity) compartment of the knee. Traditionally, unicondylar knee arthroplasty is an open procedure in which a surgeon, after exposing the knee, resects diseased or otherwise undesirable bone from the appropriate compartment of the knee, including portions of the distal femur and the proximal tibia. The distal femur and proximal tibia of the affected compartment are also shaped to receive a unicondylar knee prosthesis.

In traditional unicondylar knee arthroplasty, leg alignment requires a trial and error technique in which the surgeon makes one of the distal femoral cut and the proximal tibial cut and thereafter selects the location of the other of the distal femoral cut and the proximal tibial cut based on experience and the knowledge that tibial prostheses are available in a limited number of thicknesses. Typically, the proximal tibial cut is made so as to remove the least amount of the proximal tibia, while ensuring sufficient removal of diseased or otherwise undesirable bone. The remaining femoral cuts are made to complete shaping of the femur to receive a femoral prosthesis. After the femoral and tibial cuts are complete, the femoral prosthesis and the tibial prosthesis, or provisional versions thereof, are temporarily implanted and leg alignment is reviewed by the surgeon. If the tibial prosthesis does not include an integral bearing component, then a discrete bearing component is also implanted. To adjust leg alignment, the surgeon can replace the tibial prosthesis, or bearing component with an alternative tibial prosthesis, or bearing component having an increased or decreased thickness. The surgeon may also recut the femur and/or use a different femoral implant to achieve appropriate leg alignment. The surgeon can also remove more tibial bone stock and again use the previously used tibial prosthesis, or replace the previously used tibial prosthesis with a tibial prosthesis of a different thickness. This procedure of trial and error is conducted until the surgeon believes that appropriate leg alignment and soft tissue tension has been achieved.

The traditional trial and error technique utilized in performing unicompartmental knee arthroplasty is tedious and time consuming, and may result in excessive removal of tibial and/or femoral bone. One alternative prior art technique utilizes a spacing mechanism to extend the spacing in the compartment of the knee receiving the unicondylar knee prosthesis. In this prior art technique, the compartment spacing is extended until the surgeon is happy with limb alignment. The device used to extend the knee compartment is used as a reference for a cut block through which the distal femur and proximal tibia are cut with the knee in full extension. This technique is unfavorable because many surgeons do not want to cut the tibia when the knee is in full extension for fear of damaging the popliteal structures behind the knee that are close to the bone when the knee is in full extension. When the knee is placed in flexion, the popliteal structures are drawn away from the bone to provide additional room for error in cutting the proximal tibia without damaging the popliteal structures.

What is needed in the art is a minimally invasive method and apparatus for creating correct limb alignment in unicondylar knee arthroplasty.

What is additionally needed in the art is a cut guide apparatus through which distal femoral and proximal tibial cuts having a predetermined spacing can be made and which allows for resection of the proximal tibia in flexion.

SUMMARY OF THE INVENTION

The present invention provides a minimally invasive procedure for creating correct limb alignment in unicondylar knee arthroplasty. Depending on which compartment of the knee is receiving a prosthesis, either a medial, or a lateral parapatellar incision is made to expose the knee joint. The incision used in the method of the present invention is smaller than the incision of the traditional open procedure. After developing the wound, the anterior tibial boss of the relevant compartment of the knee is resected and an adjustable alignment block in accordance with the present invention is inserted into the relevant compartment of the knee.

The adjustable alignment block of the present invention includes a femoral paddle for contacting the femur and a tibial paddle for contacting the tibia. In use, the femoral and tibial paddles are inserted into the relevant compartment of the knee after removal of the anterior tibial boss. The apparatus of the present invention includes an alignment tower attachable to the adjustable alignment block and having an alignment rod receiving end that is positioned between the condyles of the knee when the alignment tower is attached to an adjustable alignment block inserted into a compartment of the knee. The alignment rod receiving end of the alignment tower includes a pair of apertures, one for receiving a femoral alignment rod, and the other for receiving a tibial alignment rod. When inserted in the appropriate apertures of the alignment rod receiving end, the femoral and tibial alignment rods have an end positioned between the condyles of the knee and the two rods are parallel. To align the knee, the femoral alignment rod is aligned with the mechanical axis of the femur and the lower leg is moved until the tibial alignment rod aligns with the tibial mechanical axis. With joint alignment corrected, the tibial paddle of the adjustable alignment block is moved away from the femoral paddle thereof, until the femoral paddle contacts the femur and the tibial paddle concurrently contacts the tibia to maintain the knee in proper alignment, i.e., the proper balance of limb alignment and soft tissue balance. The adjustable alignment block is secured to the tibia and femur, and the alignment tower and alignment rods are then removed.

The adjustable alignment block of the present invention includes a femoral cut slot through which the distal femoral cut is made. The femoral cut slot is spaced from the femoral paddle a predetermined distance to allow for removal of the appropriate amount of femoral bone stock. With the knee in flexion, and with the femoral cut block secured to the tibia and femur, an oscillating saw or other appropriate instrument is utilized to resect the distal femur. After resection of the distal femur, the adjustable alignment block is removed, leaving a pair of headless securing devices which were used to secure the adjustable alignment block to the tibia. The headless securing devices are spaced a predetermined distance from the femoral cut slot and serve as a reference for linking the distal femoral cut to the proximal tibial cut.

A tibial cut block of the present invention is now used to resect the proximal tibia. The tibial cut block of the present invention includes a number of hole pairs sized and spaced to accommodate insertion of the headless securing devices therein. Each of the hole pairs of the tibial cut block correspond to a different implant thickness. The tibial cut block also includes a tibial cut slot through which the proximal tibial cut can be made. The tibial cut is attached to the tibia by positioning the headless securing devices into the appropriate hole pair for the desired implant, and, after making the sagittal cut in the proximal tibia, the horizontal tibial cut is made through the tibial cut slot.

An advantage of the present invention is the ability to perform a unicondylar knee arthroplasty while facilitating patient recovery due to the minimally invasive nature of the technique disclosed herein.

A further advantage of the present invention is the establishment of predetermined alignment and soft tissue balance ensuring accurate component positioning through linked parallel bone cuts on the distal femur and proximal tibia.

Another advantage of the present invention is the ability to link bone cuts on the distal femur and proximal tibia while allowing resection of the proximal tibia in flexion.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein:

FIG. 1 is a schematic depiction of a healthy knee joint having a neutral mechanical axis;

FIG. 2 is a schematic depiction of a knee joint having a varus deformity;

FIG. 5 is a perspective view illustrating use of an oscillating saw to resect the anterior tibial boss in the affected compartment of the knee;

FIG. 6 is a perspective view of an adjustable alignment block of the present invention in an open position;

FIG. 7 is a perspective view of the adjustable alignment block of FIG. 6 illustrated in a closed position;

FIGS. 9 and 10 are side plan views of the adjustable alignment block of FIGS. 6-8 illustrated in the closed and open positions, respectively;

FIGS. 21-24 are top, side, first end, and second end views of a distal telescoping rod of the present invention;

FIG. 28 is a side plan view of a minus 2 millimeter femoral spacer of the present invention;

FIG. 29 is a top plan view thereof;

FIG. 30 is a bottom plan view thereof;

FIG. 31 is a sectional view thereof taken along line 31-31' of FIG. 30;

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figures 3, 4:
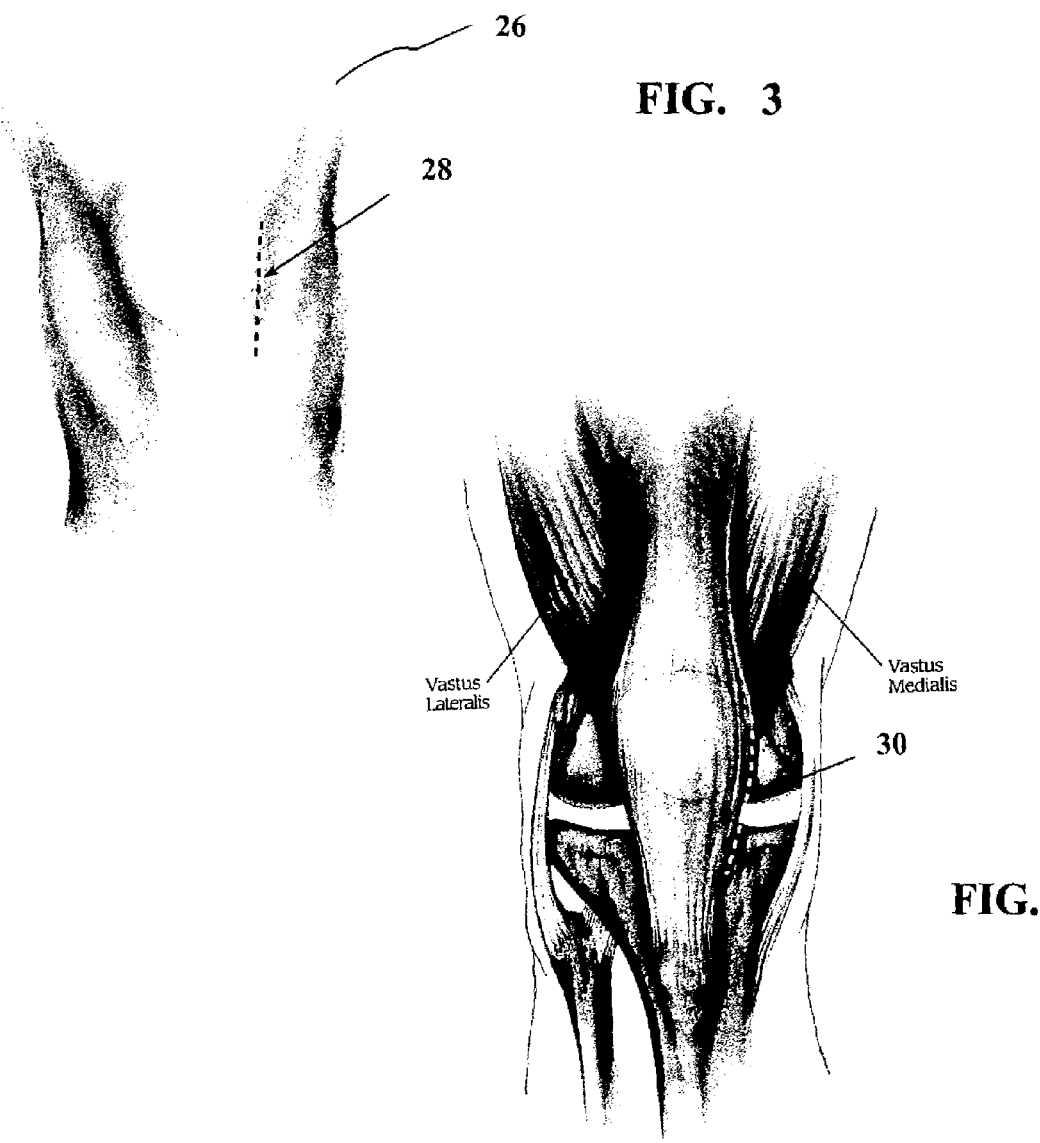
FIG. 3 is a schematic depiction of a patient's leg illustrating the incision required to perform a medial compartment unicondylar knee arthroplasty in accordance with the present invention.
FIG. 4 is a schematic depiction illustrating the bones, ligaments, and muscles of the knee area and further illustrating the capsular incision required for performing a medial compartment unicondylar knee arthroplasty in accordance with the present invention.

The description that follows refers to a medial compartment unicondylar knee arthroplasty. While described with respect to a medial compartment unicondylar knee arthroplasty, the principles of the present invention can be applied to the lateral compartment, although a slightly longer incision may be necessary when replacing the lateral compartment of the knee.

Preoperative Planning

Prior to performing a unicondylar knee arthroplasty in accordance with the present invention, weight bearing anterior/posterior and lateral radiographs of the affected knee should be taken. Further, a supine anterior/posterior radiograph showing the center of the femoral head, the knee, and as much of the tibia as possible, preferably including the ankle, should be taken. On this last X-ray, the surgeon can draw a line from the center of the femoral head to the center of the distal femur at the knee and draw a second line down the center of the tibial shaft. The angle formed by these two lines represents the angle of deformity ∀ as illustrated in FIG. 2.

FIG. 2 schematically illustrates knee joint 24 having a varus deformity. As illustrated in FIG. 2, line 20' drawn from the center of femoral head 16' to the center of distal femur 18' at knee 24 forms an angle ∀ with line 22' drawn down the center of the shaft of tibia 12'. This angle ∀ represents the angle of varus deformity of knee joint 24. FIG. 1 illustrates healthy knee joint 14. As illustrated in FIG. 1, line 20 drawn from the center of femoral head 16 to the center of distal femur 18 at knee 14 is colinear with line 22 drawn down the center of the shaft of tibia 12, representing a knee joint without deformity. If the angle of deformity ∀ is 15 degrees or greater, the patient is likely not a candidate for unicompartmental knee arthroplasty.

With the patient in supine position, the ankle area is wrapped with an elastic wrap and accessibility of the proximal femur is checked. The proximal femur must be accessible to allow for assessing the femoral head location which is used to determine the angle of deformity ∀ as illustrated in FIG. 2 and discussed above. At this point, anatomic landmarks may be utilized to identify the location of the femoral head. In one exemplary embodiment, a marker such as an EKG electrode can be positioned over the center of the femoral head to serve as a reference point. In one exemplary embodiment, the location of the femoral head is confirmed with an anterior/posterior radiograph.

Surgical Procedure

Referring to FIG. 3, incision 28 is made in patient leg 26 to expose the knee joint. Incision 28 can be made in flexion or extension according to surgeon preference. Incision 28 is, in the exemplary embodiment disclosed, a medial parapatellar incision extending six to ten centimeters from the superior pole of the patella to about two centimeters below the joint line adjacent to the tibial tubercle as illustrated in FIG. 3. If a lateral compartment unicondylar knee arthroplasty is being performed, the incision is a lateral parapatellar incision extending from the superior pole of the patella to about 2 centimeters below the joint line adjacent to the tibial tubercle. Note that FIGS. 3 and 4 illustrate a right knee, while the remaining figures of this document illustrate a left knee. The procedure of the present invention is, of course, applicable to both the right and left knees.

After making incision 28, the wound is developed to expose the joint capsule. Referring to FIG. 4, capsular incision 30 is made in the joint capsule distal to the vastus medialis in line with incision 28 to a point that exposes the anterior margin of the femoral condyle as illustrated in FIG. 4. The fat pad may be excised to facilitate visualization of the knee joint. The soft tissue is now reflected subperiosteally from the tibia along the joint line toward, but not into, the collateral ligament. In the exposed knee compartment, a portion of the anterior meniscus is removed. In one exemplary embodiment, about one third of the anterior meniscus is removed. The remainder of the meniscus will be removed after resection of the distal femur and proximal tibia.

The joint is now debrided and intercondylar osteophytes are removed to avoid impingement with the tibial spine or cruciate ligament. Furthermore, peripheral osteophytes interfering with the collateral ligaments and capsule are removed. For example, with medial compartment disease, osteophytes are commonly found on the lateral aspect of the tibial eminence.

Referring to FIG. 5, with the knee flexed, oscillating saw 32 is inserted into the exposed knee compartment and applied to tibia 12' with oscillating saw blade 36 operating to resect anterior tibial boss 34. The knee is then placed in full extension with a towel positioned under the ankle to help maintain the knee in full extension. In this position, leg alignment is passively corrected, i.e., corrected until visually appearing to be correct.

Figure 12:
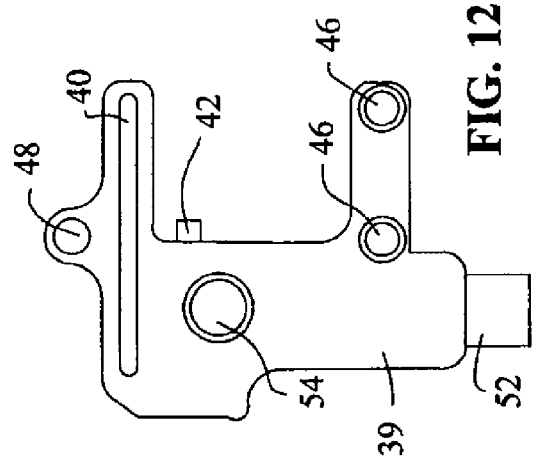
FIG. 12 is a top elevational view of the adjustable alignment block of FIGS. 6-11.
Figure 13:
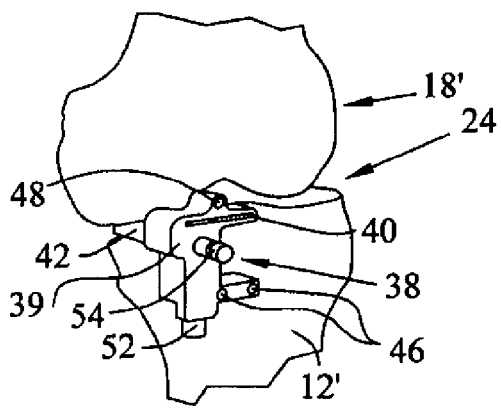
FIG. 13 is a perspective view illustrating inserting the adjustable alignment block of FIGS. 6-12 into a knee joint to facilitate correction of a varus deformity.

Referring to FIG. 13, adjustable alignment block 38 (further illustrated in FIGS. 6-12) is next positioned with femoral paddle 42 (FIG. 7) positioned between the medial femoral condyle and the portion of the tibia from which anterior tibial boss 34 is removed. Prior to insertion of adjustable alignment block 38, tibial paddle 44 is positioned in the closed position as illustrated in FIGS. 7 and 9.

Figure 11:
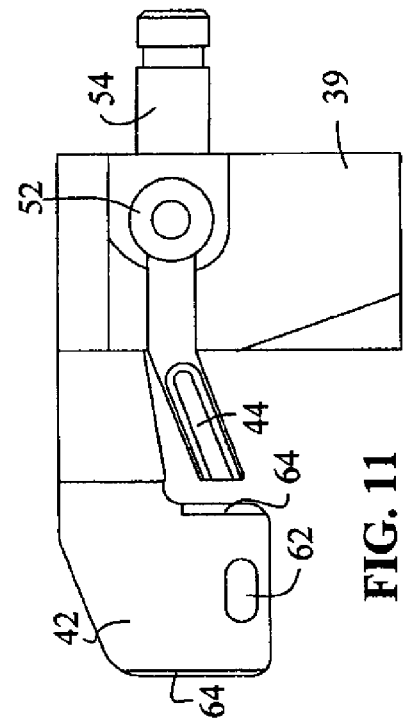
FIG. 11 is a distal elevational view of the adjustable alignment block of FIGS. 6-10.

Referring to FIGS. 8-12, adjustable alignment block 38 includes body 39 having femoral paddle 42 extending therefrom. As illustrated in FIG. 11, femoral paddle 42 includes opposing spacer bevels 64 and spacer slot 62. Spacer bevels 64 and spacer slot 62 are utilized in conjunction with minus 2 millimeter femoral spacer 56 as further described hereinbelow. Opposite femoral paddle 42, alignment tower boss 54 extends from body 39 of adjustable alignment block 38. Body 39 includes apertures 46, 48 formed therein for affixing adjustable alignment block 38 to the femur and tibia as is further described hereinbelow. Body 39 of adjustable alignment block 38 further includes femoral cut slot 40 through which the distal femoral cut will be made as further described hereinbelow.

Figure 8:
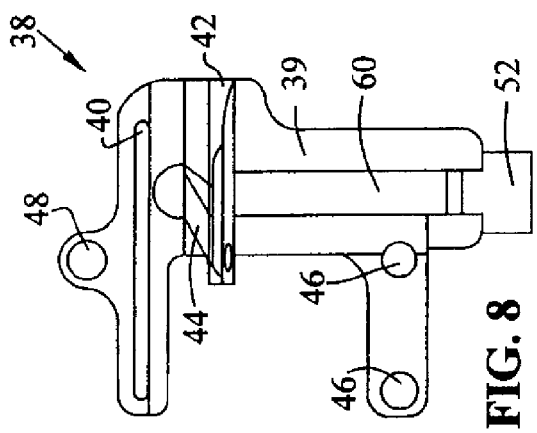
FIG. 8 is a bottom elevational view of the adjustable alignment block of FIGS. 6 and 7 illustrated in a closed position.

Adjustable alignment block 38 further includes tibial paddle groove 50 in which tibial paddle 44 is positioned. Tibial paddle groove 50 guides movement of tibial paddle 44 between the closed position of adjustable alignment block 38 illustrated in FIGS. 7 and 9 to the open position thereof illustrated in FIGS. 6 and 10. As illustrated in FIG. 8, threaded shaft 60 is rotatably positioned in an elongate aperture of body 39 of adjustable alignment block 38. Tibial paddle actuation knob 52 is secured to threaded shaft 60 and extends from body 39 of adjustable alignment block 38 to allow for actuation of threaded shaft 60. Tibial paddle 44 includes an end positioned between adjacent threads of threaded shaft 60 so that rotation of tibial paddle actuation knob 52, which causes rotation of threaded shaft 60 actuates tibial paddle 44 between the opened and closed positions.

Adjustable alignment block 38 illustrated herein is a left medial/right lateral adjustable alignment block. An alternative alignment block can be utilized for a right medial unicondylar knee arthroplasty and a left lateral unicondylar knee arthroplasty. Such an alternative alignment block will be a mirror image of alignment block 38 illustrated herein. Referring to FIG. 12, the mirror image alignment block would include tibial affixment apertures 46 positioned to the left of tibial paddle actuation knob 52. Furthermore, in the alternative embodiment adjustable alignment block, femoral cut slot 40 would extend further to the left of tibial paddle actuation knob 52 from the perspective of FIG. 12.

If the joint is too tight to allow insertion of femoral paddle 42 of adjustable alignment block 38 into knee 24 as described above, additional anterior tibial bossing should be removed, as described with reference to FIG. 5, to create more space for inserting alignment block 38. Patellar osteophytes can be removed for better exposure. Advantageously, the technique of the present invention does not require movement of the patella. Adjustable alignment block 38 will be used to hold the joint in proper alignment and will further be used as a resection guide when making the distal femoral cut as is fully described hereinbelow.

Figure 14:
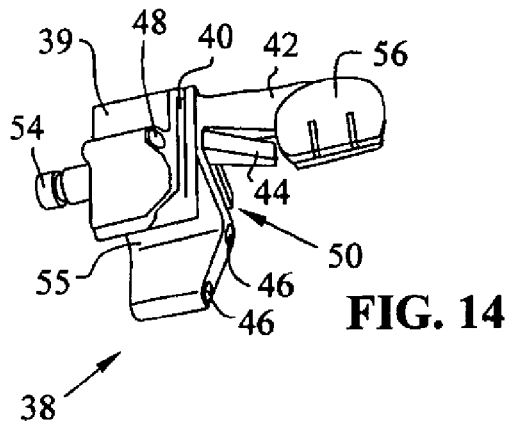
FIG. 14 is a perspective view of the adjustable alignment block of FIGS. 6-12, with a minus 2 millimeter femoral spacer secured thereto.

If there is significant erosion of the femoral condyle, two millimeters less bone may be resected from the distal femoral condyle. In such a case, minus two millimeter distal femoral spacer 56 (FIGS. 28-31) will be positioned atop femoral paddle 42 of adjustable alignment block 38 as illustrated in FIG. 14. With minus two millimeter distal femoral spacer 56 attached to femoral paddle 42 of adjustable alignment block 38, femoral cut slot 40 will be moved two millimeters distally with respect to distal femur 18' from the position illustrated in FIG. 13, i.e., a position in which minus two millimeter distal femoral spacer 56 is not secured to femoral paddle 42 of adjustable alignment block 38. Therefore, two millimeters less femoral bone will be resected when an oscillating saw is positioned through femoral cut slot 40 when minus two millimeter distal femoral spacer is utilized.

Minus 2 millimeter femoral spacer 56 is illustrated in detail in FIGS. 28-31. As illustrated in FIG. 28, minus 2 millimeter femoral spacer 56 has height H measuring 2 millimeters. With this in mind, with minus 2 millimeter femoral spacer 56 positioned atop femoral paddle 42 as illustrated in FIG. 14, cut slot 40 will be moved 2 millimeters distally along femur 18' relative to its position when adjustable alignment block 38 is positioned in knee joint 24 without minus 2 millimeter femoral spacer 56.

Femoral spacers of varying heights may be utilized in accordance with the present invention to adjust the depth of the distal femoral resection. Minus 2 millimeter femoral spacer 56 is illustrated in detail in FIGS. 28-31. As illustrated in FIG. 31, femoral spacer 56 includes dovetails 84 extending from a lower surface thereof to effect securement of distal femoral spacer 56 to femoral paddle 42 of adjustable alignment block 38. As illustrated in FIG. 11, femoral paddle 42 of adjustable alignment block 38 includes opposing spacer bevels 64 which facilitate expansion of dovetails 84 of minus 2 millimeter femoral spacer 56 to allow for positioning of minus 2 millimeter femoral spacer 56 atop femoral paddle 42. Furthermore, referring to FIGS. 29 and 30, minus 2 millimeter femoral spacer 56 includes a pair of expansion slots 58 facilitating outward expansion of dovetails 84 when securing minus 2 millimeter femoral spacer 56 to femoral paddle 42 of adjustable alignment block 38. When minus 2 millimeter femoral spacer 56 is secured to femoral paddle 42, adjustable alignment block protrusion 66 thereof fits within spacer slot 62 of femoral paddle 42 to prevent sliding of minus 2 millimeter femoral spacer 56 with respect to femoral paddle 42. To remove minus 2 millimeter femoral spacer 56 from femoral paddle 42, a pry bar is inserted therebetween to urge adjustable alignment block protrusion 66 out of spacer slot 62 of femoral paddle 42. Minus 2 millimeter femoral spacer 56 can then be slid from engagement with femoral paddle 42.

Figure 19:
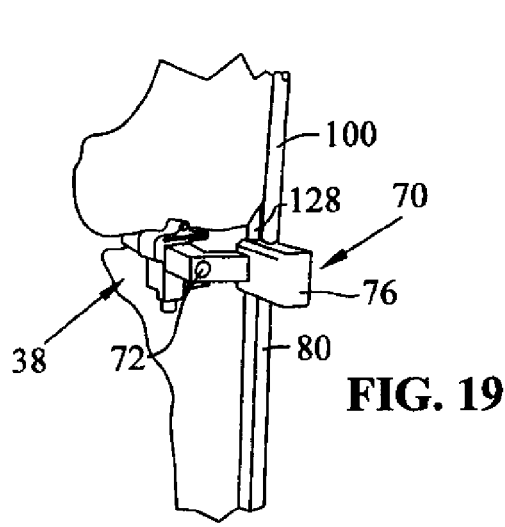
FIG. 19 is a partial perspective view of the knee joint of FIG. 13, with an adjustable alignment block positioned therein, and with an alignment tower as well as femoral and tibial alignment rods secured to the adjustable alignment block.
Figure 18:
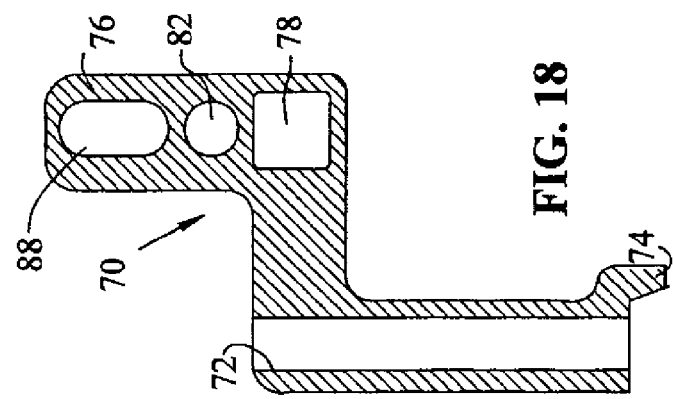
FIG. 18 is a sectional view thereof taken along line 18-18' of FIG. 16.
Figure 17:
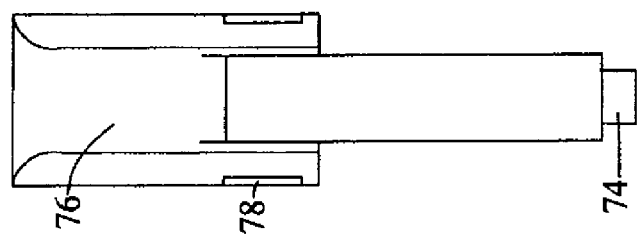
FIGS. 15-17 are side, top, and end views, respectively of an alignment tower of the present invention.
Figure 16:
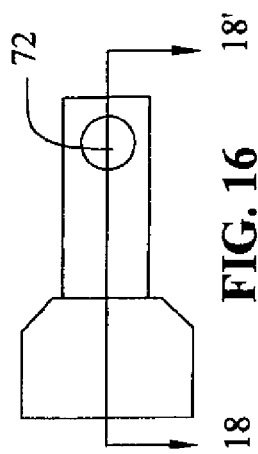
Figure 15:
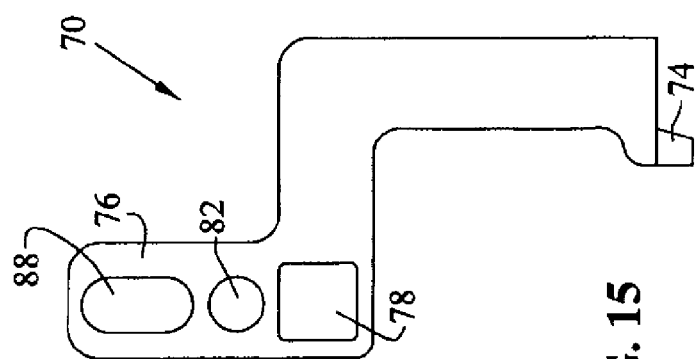

With adjustable alignment block 38 positioned with femoral paddle 42 (with or without minus two millimeter distal femoral spacer 56 secured thereto) positioned in the space created in the affected compartment as illustrated in FIG. 13, alignment tower 70, which is illustrated in detail in FIGS. 15-18, is secured to adjustable alignment block 38 as illustrated in FIG. 19. Referring to FIG. 18, alignment tower 70 includes boss aperture 72 sized for placement of alignment tower boss 54 therein when alignment tower 70 is secured to adjustable alignment block 38. Alignment tower 70 further includes alignment protrusion 74 which abuts base 55 of adjustable alignment block 38 when alignment tower 70 is secured to adjustable alignment block 38. Alignment protrusion 74 is wedge shaped as illustrated in FIGS. 15 and 18. As alignment tower boss 54 of adjustable alignment block 38 traverses boss aperture 72 of alignment tower 70, alignment protrusion 74 contacts base 55 of adjustable alignment block 38 and, owing to its wedge shape, locks alignment tower 70 to adjustable alignment block 38. With alignment tower boss 54 positioned within boss aperture 72, and alignment protrusion 74 abutting base 55, alignment tower 70 is secured to adjustable alignment block 38 and will not rotate relative thereto. With adjustable alignment block 38 positioned as illustrated in FIGS. 13 and 19, and with alignment tower 70 secured thereto as illustrated in FIG. 19, alignment rod receiving end 76 of alignment tower 70 is located between the condyles of distal femur 18'.

Figure 20:
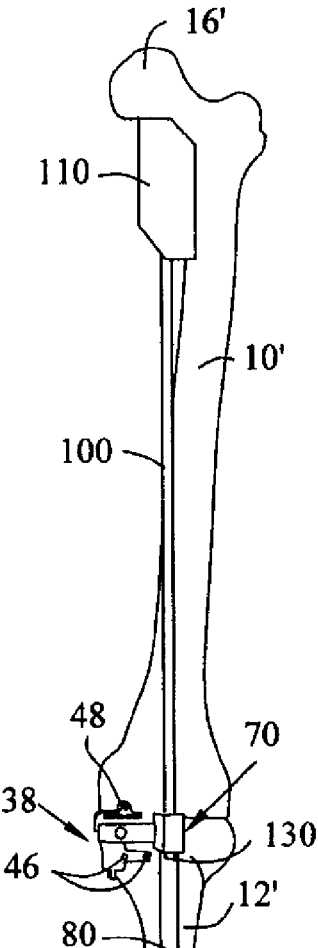
FIG. 20 is a plan view illustrating use of the alignment device of the present invention to facilitate correction of limb alignment in a joint having a varus deformity.

The alignment device is now fully assembled as illustrated in FIG. 20. With adjustable alignment block 38 and alignment tower 70 positioned as illustrated in FIG. 19, first end 128 of square alignment rod 80 is inserted into square alignment rod aperture 78 (FIG. 15) of alignment tower 70 as illustrated in FIGS. 19 and 20. The opposite end of square alignment rod 80 is thereafter inserted into elongate square alignment rod aperture 92 (FIG. 24) of distal telescoping rod 90 (FIGS. 21-14) as illustrated in FIG. 20.

Figure 27:
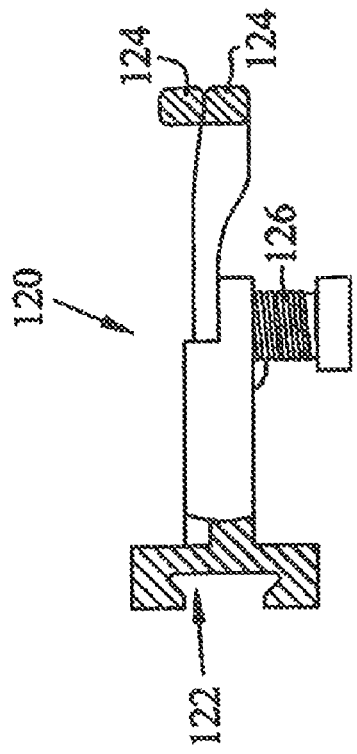
FIG. 27 is a sectional view thereof taken along line 27-27' of FIG. 26.
Figure 26:
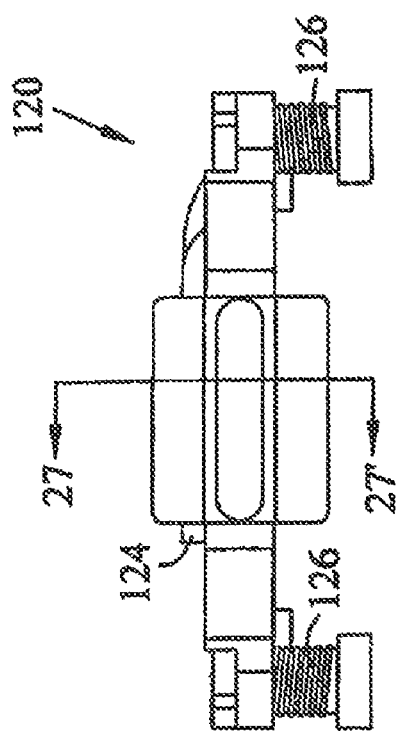
FIG. 26 is a top plan view thereof.
Figure 25:
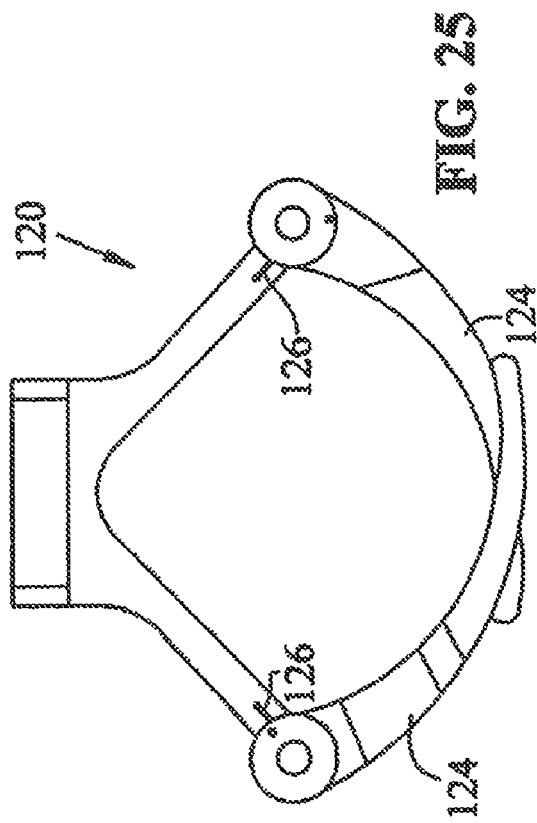
FIG. 25 is an end plan view of an ankle clamp of the present invention.

Prior to inserting square alignment rod 80 into elongate square alignment rod aperture 92 (FIG. 24) of distal telescoping rod 90, ankle clamp 120 (FIGS. 25-27) is connected to distal telescoping rod 90. Referring to FIG. 27, ankle clamp 120 includes dovetail channel 122 sized to accommodate dovetail 94 (FIG. 22) of distal telescoping rod 90. As illustrated in FIG. 22, distal telescoping rod 90 includes ankle clamp retaining knob 98 to temporarily secure ankle clamp 120 to distal telescoping rod 90. As illustrated in FIGS. 22-24, ankle clamp retaining knob 98 is secured to ankle clamp retaining rod 102 which is threadedly engaged in ankle clamp retaining cylinder 104 and extends through dovetail 94. With dovetail 94 positioned in dovetail channel 122, ankle clamp retaining knob 98 is rotated to force an end of ankle clamp retaining rod 102 to extend from the bottom surface of dovetail 94 and create an interference fit between dovetail 94 and dovetail channel 122. Ankle clamp 120 may, in one exemplary embodiment, include a channel for accommodating the end of ankle clamp retaining rod 102 extending below dovetail 94.

Figure 36:
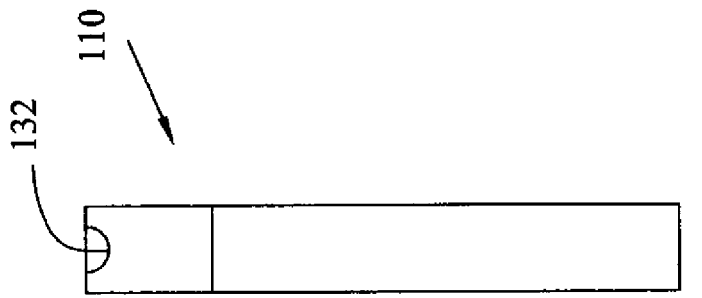
FIG. 36 is a side view thereof.
Figure 35:
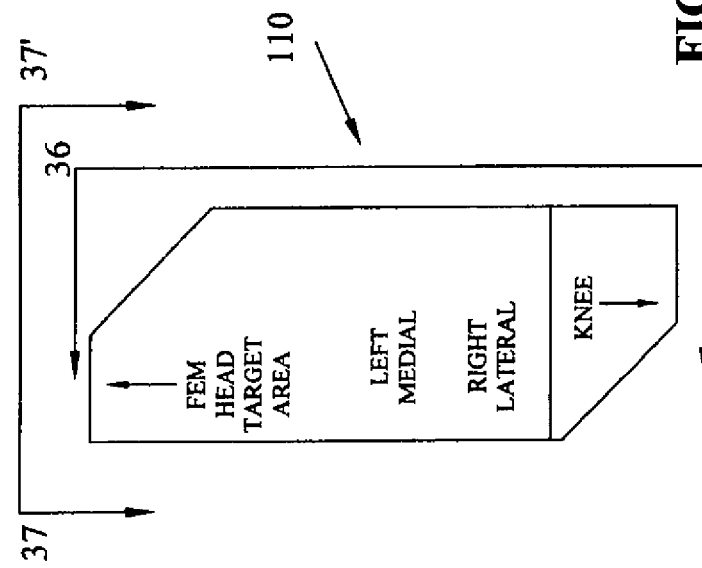
FIG. 35 is a top plan view of a targeting guide of the present invention.
Figure 37:
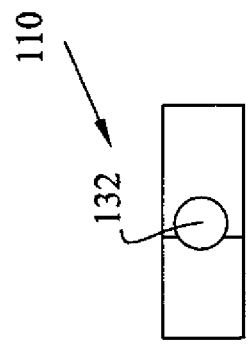
FIG. 37 is an end view thereof.

With ankle clamp 120 temporarily secured to distal telescoping rod 90, spring arms 124 are opened against the biasing force of springs 126 and are positioned around the ankle proximal to the malleoli, as square alignment rod 80 is inserted into elongate square alignment rod aperture 92 of distal telescoping rod 90. Ankle clamp 120 advantageously prohibits coronal rotation of the spacing apparatus of the present invention. As illustrated in FIGS. 19 and 20, round alignment rod 100 is then inserted in round alignment rod aperture 82 (FIGS. 15 and 18) of alignment tower 70, with the remainder of round alignment rod 100 extending proximally as illustrated in FIG. 20. In an alternative embodiment, round alignment rod 100 is inserted in alternative round alignment rod aperture 88. As illustrated in FIGS. 15 and 18, alternative round alignment rod aperture 88 is elliptical. Alternative round alignment rod aperture 88 is utilized when the alignment apparatus of the present invention is used with a patient having a large or obese thigh. Targeting guide 110 is then slid onto the proximal end of round alignment rod 100 to complete the assembly of the alignment apparatus as illustrated in FIG. 20. With the alignment apparatus assembled and connected to the patient as illustrated in FIG. 20, first end 128 of square alignment rod 80 and first end 130 of round alignment rod 100 are located between the condyles of distal femur 18'. Targeting guide 110 is more fully illustrated in FIGS. 35-37. As illustrated in FIGS. 36 and 37, targeting guide 110 includes round alignment rod aperture 132 into which round alignment rod 100 is positioned when the alignment apparatus is fully assembled as illustrated in FIG. 20. As illustrated in FIG. 35, targeting guide 110 includes anterior marking indicating proper positioning thereof. As illustrated in FIG. 35, targeting guide 110 includes markings indicating left medial/right lateral, indicating that with this surface oriented anteriorly, targeting guide 110 is useful when performing a left medial unicondylar knee arthroplasty, or a right lateral unicondylar knee arthroplasty. The opposite side of targeting guide 110 includes markings indicating right medial/left lateral, indicating that with the opposite marked surface oriented anteriorly, targeting guide 110 is useful when performing a right medial unicondylar knee arthroplasty, or a left lateral unicondylar knee arthroplasty. On the opposite side of targeting guide 110, the femoral head target area is positioned right of center.

Alternatively, the alignment assembly can be assembled before adjustable alignment block 38 is inserted into the joint. In this embodiment, spring arms 124 of ankle clamp 120 are moved against the biasing force of springs 126 into an open position to accommodate placement about the patient's ankle and are positioned about the patient's ankle as femoral paddle 42 of adjustable alignment block 38 is inserted into the compartment of the knee undergoing unicondylar knee arthroplasty. Specifically, alignment tower 70 can be positioned atop adjustable alignment block 38, with alignment tower boss 54 of adjustable alignment block 38 inserted into boss aperture 72 of alignment tower 70, and with alignment protrusion 74 abutting base 55 of adjustable alignment block 38. With alignment tower 70 secured to adjustable alignment block 38, ankle clamp 120 is slid onto dovetail 94 of distal telescoping rod 90 with ankle clamp retaining knob 98 tightened to temporarily hold ankle clamp 120 to distal telescoping rod 90. An end of square alignment rod 80 is then inserted into distal telescoping rod 90, and first end 128 of square alignment rod 80 is positioned through square alignment rod aperture 78 (FIG. 15) of alignment tower 70. With leg alignment passively corrected, the joint is held open and femoral paddle 42 of adjustable alignment block 38 is inserted into the space created in the effected compartment of the knee, with the ankle clamp positioned above the ankle. At this point, spring arms 124 are moved against the biasing force of springs 126 into an open position and placed about the ankle proximal to the malleoli to complete securement of the alignment apparatus to the patient. Alternatively, as indicated above, the ankle clamp may be secured about the ankle concurrent with introduction of femoral paddle 42 of adjustable alignment block 38 into the effected compartment of the knee.

Joint Alignment

With the alignment apparatus positioned as illustrated in FIG. 20, ankle clamp retaining knob 98 is loosened to allow for mediolateral adjustment of distal telescoping rod 90. With ankle clamp retaining knob 90 loosened to allow for relative movement of distal telescoping rod 90 with respect to ankle clamp 120, distal tip 106 of distal telescoping rod 90 is moved until it is positioned about 5-10 millimeters medial to the midpoint between the palpable medial and lateral malleoli. For the medial compartment arthroplasty disclosed herein, distal tip 106 should point to the second metatarsal. When distal tip 106 of distal telescoping rod 90 is properly positioned as indicated above, ankle clamp retaining knob 98 is tightened to secure distal telescoping rod in this mediolateral position. Proximally, the longitudinal axis of square alignment rod 80 (and, consequently, distal telescoping rod 90) should lie just medial to the midpoint of the tibial tubercle and be centered over the intercondylar eminence. Distal telescoping rod 90 and square alignment rod 80 are positioned parallel to the anterior tibial crest by loosening elevation adjustment knob 108 and adjusting the height of square alignment rod tube 112 and, consequently, square alignment rod 80 until they are parallel to the anterior tibial crest and thereafter tightening elevation adjustment knob 108 to hold the distal alignment apparatus in the proper position.

The leg is now positioned in the desired alignment by moving the leg until targeting guide 110 points toward the center of the femoral head. Over correction should be avoided. It is preferable to align the limb in a slight varus for medial compartment arthroplasty or in slight valgus for a lateral compartment arthroplasty. With this in mind, the femoral head target area marked on targeting guide 110 is offset to the left of the longitudinal axis of round alignment rod aperture 132 as illustrated in FIG. 35. This offset allows for the desired slight undercorrection in limb alignment. With the limb properly aligned, actuation knob 52 is turned to actuate adjustable alignment block 38 from the closed position illustrated in FIGS. 9 and 7 into an open position (e.g., the position illustrated in FIGS. 6 and 10), with opening discontinuing when tibial paddle 44 engages the proximal tibia and the joint space is filled. Adjustable alignment block 38 is utilized to hold the joint in alignment.

With the joint held in proper alignment, headless screws 160 (see, e.g., FIG. 39) are inserted through tibial affixment apertures 46 of adjustable alignment block 38 and driven into tibia 12', leaving the screws proud of adjustable alignment block 38. If preferred, headless holding pins can be used in place of the headless screws, but in this embodiment holes must be predrilled to accept the pins without drilling down to the entire length of the pin that will be inserted, as this may compromise pin fixation. A headed screw is then inserted through femoral affixment aperture 48 in adjustable alignment block 38 and driven into distal femur 18'. The headed screw may be hand tightened into femur 10' to avoid over torquing and the consequent stripping of the bone stock. At this point alignment is verified, and, if unchanged, alignment tower 70, round alignment rod 100, square alignment rod 80, distal telescoping rod 90, and ankle clamp 120 are removed.

With adjustable alignment block 38 secured to femur 10' and tibia 12' (see, e.g., FIG. 20), an oscillating or reciprocating blade is inserted through femoral cut slot 40 of adjustable alignment block 38 and utilized to resect the distal femoral condyle. In one exemplary embodiment, the distal femoral cut is started with adjustable alignment block 38 secured to both the tibia and the femur, and is completed by removing the headed screw positioned through femoral affixment aperture 48, and placing the knee in flexion. If the distal femoral cut is finished with adjustable alignment block 38 secured to femur 10' and tibia 12', then the headed femoral screw is removed from femoral affixment aperture 48 after the distal femoral resection is complete.

After removing the femoral screw, adjustable alignment block 38 is actuated toward the closed position illustrated in FIGS. 7 and 9 by rotating actuation knob 52 in a counter-clockwise direction. Adjustable alignment block 38 is then removed with, e.g., pin pliers, leaving the headless screws 160 in tibia 12'. The headless screws provide the link between the distal femoral cut and the tibial plateau cut.

Figure 34:
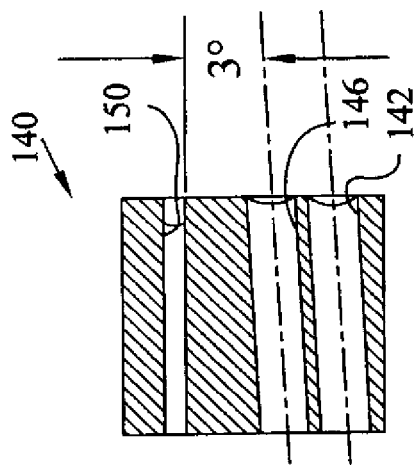
FIG. 34 is a sectional view thereof taken along line 34-34' of FIG. 32.
Figure 32:
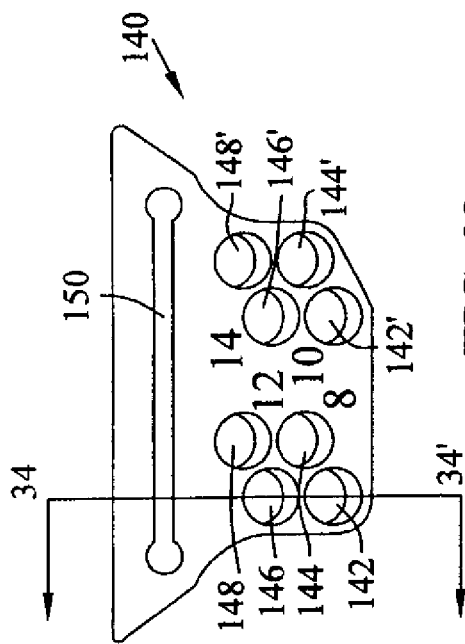
FIG. 32 is a top plan view of a tibial cut block of the present invention.
Figure 33:
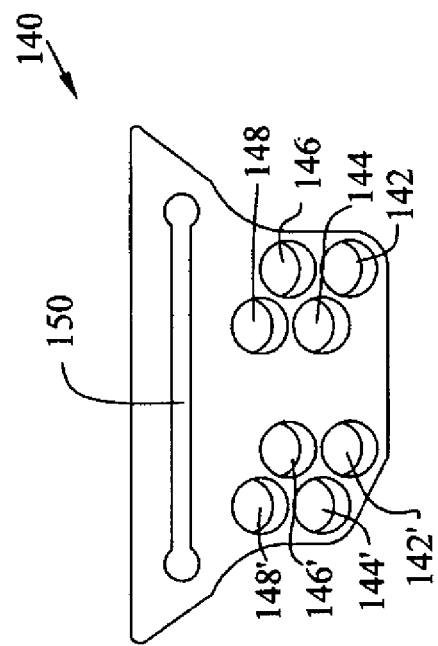
FIG. 33 is a bottom plan view thereof.

Tibial cut block 140 illustrated in FIG. 32-34 is next utilized to guide tibial resection. As illustrated in FIG. 32, tibial cut block 140 includes hole pairs 142/142', 144/144', 146/146', and 148/148'. Each hole pair is spaced to accommodate insertion of headless screws 160 positioned through tibial affixment apertures 46 of adjustable alignment block 38 and left in tibia 12' as described above. In this way, hole pairs 142/142', 144/144', 146/146', and 148/148' are used in conjunction with resection slot 150 to link the tibial cut to the distal femoral cut. As illustrated in FIG. 34, the longitudinal axes of holes 142 and 146 form a three degree angle with resection slot 150, allowing for a three degree tibial slope. It is contemplated that tibial cut blocks in accordance with the present invention can provide varying tibial slope, including nine, seven, five, or zero degrees of tibial slope.

As illustrated in FIG. 32, hole pair 142/142' is marked 8 on tibial cut block 140. Similarly, the remaining hole pairs are marked 10, 12, and 14. These hole pair designations correspond to the size of the tibial prosthetic implant, i.e., the tibial component and the bearing surface. While the exemplary embodiment includes hole pairs marked 8, 10, 12, and 14, it is contemplated that a tibial cut block in accordance with the present invention could include additional cut depths corresponding to tibial prostheses of alternative thicknesses. Initially, the headless screws protruding from tibia 12' are inserted through hole pair 142/142' corresponding to an 8 millimeter tibial articular surface, i.e., the minimum tibial resection necessary for an 8 millimeter tibial articular surface. Positioning the headless tibial screws through a hole pair of the tibial cut block aligns resection slot 150 substantially perpendicular to the mechanical axis of the knee and substantially parallel to the distal femoral cut. If a tibial cut block providing a tibial slope is utilized, then the size designations reference the middle of the tibial resection, with the middle being measured anterior to posterior, i.e., along a line contained in a sagittal plane.

After tibial cut block 140 is positioned over the headless tibial screws, the knee is flexed. If skin tension affects the alignment of tibial cut block 140, then the incision may be lengthened. In one exemplary embodiment, a resection guide can be inserted through resection slot 150 to help verify that the chosen tibial resection will be adequate. If the resection guide indicates that an insufficient amount of bone will be resected, or if a thicker articular surface is desired, tibial cut block 140 can be removed from engagement with the headless tibial screws and replaced using the next hole pair, i.e., hole pair 144/144'. A resection guide can again be utilized to help verify that the tibial resection will be adequate and tibial cut block 140 can be repositioned in the next hole pair as necessary.

Figure 38:
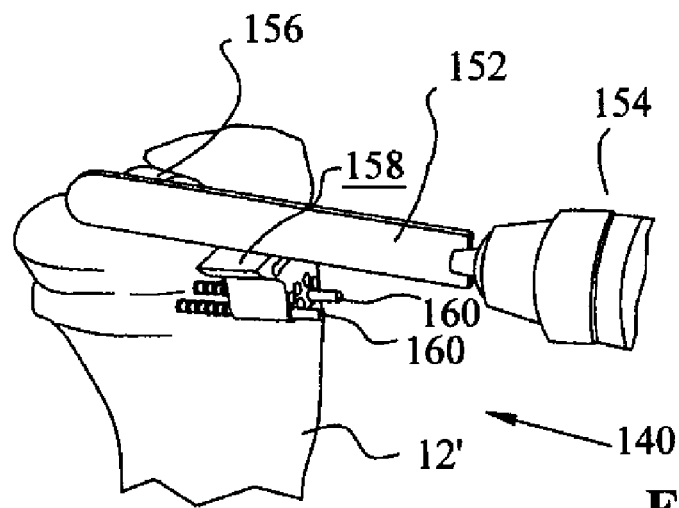
FIG. 38 is a perspective view illustrating use of a reciprocating saw to make the sagittal cut in the relevant knee compartment.

Once tibial cut block 140 is properly positioned, with headless tibial screws 160 extending through a hole pair thereof, the tibia is resected to receive a tibial implant. When resecting the femur, a retractor can be inserted medially to protect the medial collateral ligament. As illustrated in FIG. 38, the sagittal cut in tibial 12' can be made free hand. With the knee flexed, blade 152 of reciprocating saw 154 is positioned adjacent tibial eminence 156 in the affected compartment. As illustrated in FIG. 38, blade 152 of reciprocating saw 154 is positioned substantially parallel to the tibial eminence in the anterior/posterior plane. With blade 152 in position as illustrated in FIG. 38, a cut is made in the tibia along the medial edge of the tibial eminence until blade 152 contacts proximal surface 158 of tibial cut block 140. Proximal surface 158 is utilized as a guide to determine the anterior/posterior slope of the sagittal cut. Cutting to proximal surface 158 of tibial cut block 140 leaves approximately 3-4 millimeters of unresected bone of the sagittal cut. Tibial cut block 140 can be manually held in place against the bone during tibial resection, or, alternatively, one or a pair of hemostats can be clamped to headless tibial screws 160 in position abutting tibial cut block 140 to hold tibial cut block 140 flush against tibia 12'.

Optionally, tibial cut block 140 may be repositioned on headless tibial screws 160 to a hole pair that is 4 millimeters above the hole pair that will be used for the horizontal cut when making the sagittal cut. For example, if the hole pair corresponding to an 8 millimeter cut, i.e., hole pair 142/142' is determined to be the appropriate resection level, then tibial cut block 140 can be repositioned with headless tibial screws 160 positioned through hole pair 146/146' corresponding to a 12 millimeter resection. Repositioning the cut block to a pair of holes 4 millimeters above the holes desired for the horizontal cut will place proximal surface 158 of tibial cut block 140 even with the desired proximal resection level and provide a mechanical stop for the sagittal cut. Note that in the exemplary embodiment disclosed, this option is only available when an 8 millimeter or 10 millimeter implant cut depth is the desired horizontal resection level.

Figure 39:
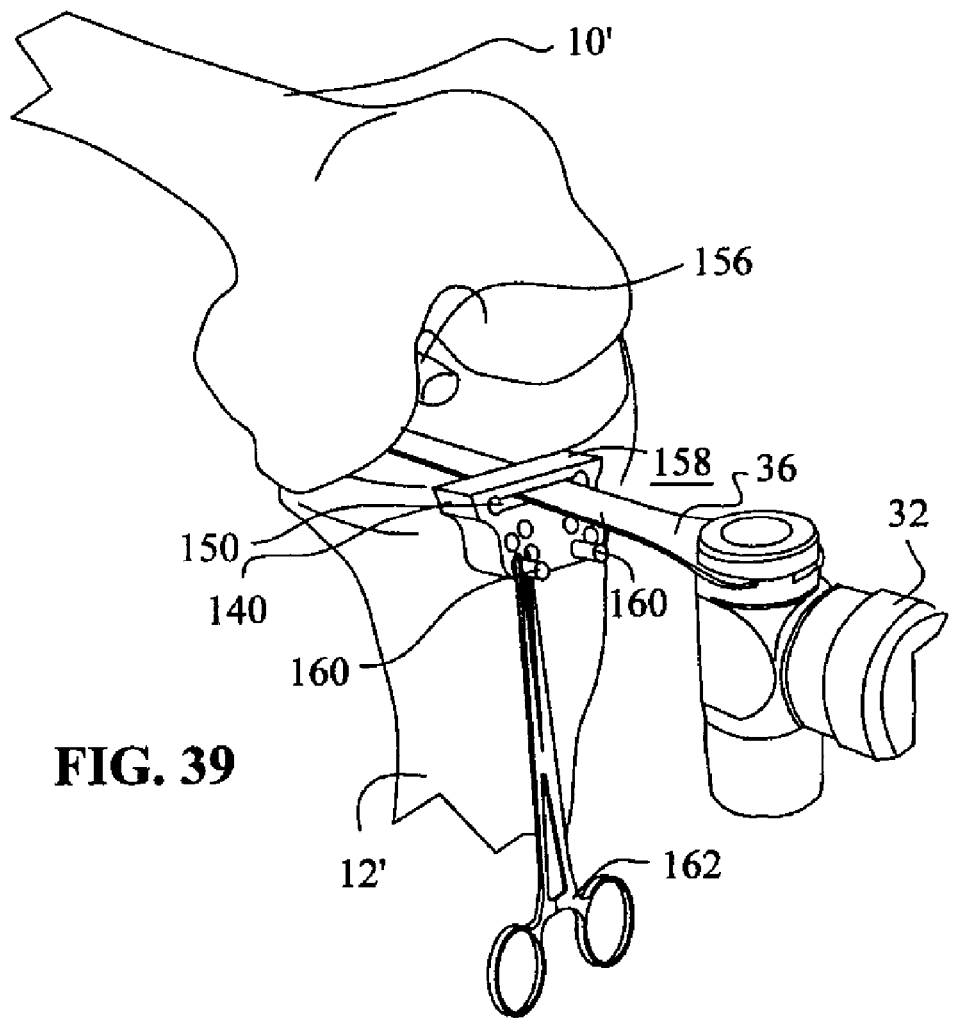
FIG. 39 is a perspective view illustrating use of an oscillating saw to resect the proximal tibia.

FIG. 39 illustrates hemostat 162 clamped to lateral tibial headless screw 160 to secure tibial cut block 140 flush against tibia 12'. As illustrated in FIG. 39, oscillating saw 32 is utilized to make the proximal tibial cut. As illustrated in FIG. 39, oscillating saw blade 36 is inserted through resection slot 150 of tibial cut block 140 to make the proximal tibial cut. When making the proximal tibial cut in this fashion, care should be taken to avoid undercutting tibial eminence 156. After the horizontal proximal tibial resection is complete, tibial cut block 140 and headless tibial screws 160 are removed. And, if the sagittal cut is unfinished, this cut is completed and the resected tibial bone fragment is removed.

The remaining meniscus can now be removed and a femoral cut guide referencing the distal femoral cut made through femoral cut slot 40 of adjustable alignment box 38 can be utilized to complete shaping of femur 10'. Provisional femoral and tibial implants are now used to perform a trial reduction and final implants are subsequently seated.

In an alternative embodiment of the present invention, the tibial cuts can be first made by aligning the joint with the alignment apparatus described above and positioning headless tibial screws 160 through tibial affixment apertures 46 of adjustable alignment block 38, but not utilizing a headed screw to secure adjustable alignment block 38 to femur 10'. With headless tibial screws 160 secured in tibia 12', the alignment apparatus is removed, including adjustable alignment block 38 and tibial cut block 140 is utilized to resect the tibia as described above. When tibial resection is complete, adjustable alignment block 38 is repositioned over headless tibial screws 60 (FIGS. 38 and 39) with the alignment apparatus reassembled as illustrated in FIG. 20 to facilitate limb alignment. After appropriate limb alignment is achieved the headed femoral screw is positioned through femoral affixment aperture 48 of adjustable alignment block 38 as described above and the distal femur is resected through femoral cut slot 40 as described above.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method of linking a proximal tibial cut made with a tibial cut guide and a distal femoral cut made with a femoral cut guide, comprising:

aligning a femur and a tibia to create a desired alignment securing the femoral cut guide to the femur, the femoral cut guide including a femoral cut slot through which the distal femoral cut can be made;

securing a reference to the tibia, said reference spaced a predetermined distance from said femoral cut slot;

removing said femoral cut guide, leaving said reference secured to the tibia;

connecting the tibial cut guide to said reference, the tibial cut guide including a tibial cut slot through which the proximal tibial cut can be made, wherein said reference links the proximal tibial cut to the distal femoral cut; and placing the knee in flexion and thereafter resecting the proximal tibia using said tibial cut guide.

2. The method of claim 1, wherein said femoral cut guide includes a pair of tibial reference apertures, wherein said reference comprises a pair of reference posts and wherein said step of securing a reference to the tibia comprises the step of securing said reference posts to the tibia through said reference apertures.

3. The method of claim 2, wherein said reference posts comprise headless pins.

4. The method of claim 2, wherein said reference posts comprise headless screws.

5. The method of claim 1, wherein said step of aligning a femur and a tibia to create a desired alignment comprises:

providing an alignment structure;

connecting the alignment structure with the femoral cut guide and aligning the alignment structure relative to the tibia and the femur and wherein said method further comprises:

disconnecting the alignment structure from the femoral cut guide before said step of securing a reference to the tibia, whereby said tibial cut guide is aligned relative to the tibia solely by the reference.

6. The method of claim 1, wherein said step of securing a reference to the tibia comprises guiding the reference with the femoral cut guide until the reference is secured to the tibia.

* * * * *

UNITED STATES PATENT AND TRADEMARK OFFICE
CERTIFICATE OF CORRECTION

PATENT NO.        : 7,842,039 B2                                    Page 1 of 1
APPLICATION NO.   : 11/456303
DATED             : November 30, 2010
INVENTOR(S)       : Robert A. Hodorek et al.

It is certified that error appears in the above-identified patent and that said Letters Patent is hereby corrected as shown below:

Title page, item [75] Fourth Inventor's name is:   Paul L. Saenger

Signed and Sealed this
First Day of February, 2011

David J. Kappos
*Director of the United States Patent and Trademark Office*